United States Patent
Bell et al.

[11] Patent Number: 4,917,107
[45] Date of Patent: * Apr. 17, 1990

[54] ENDOTRACHEAL TUBE/STETHOSCOPE COMBINATION

[75] Inventors: Floyd R. Bell, Lexington; Thomas H. McKay, Flatwoods, both of Ky.

[73] Assignee: Medi-Tube Corporation, Lexington, Ky.

[*] Notice: The portion of the term of this patent subsequent to Feb. 26, 2002 has been disclaimed.

[21] Appl. No.: 845,959

[22] Filed: Mar. 31, 1986

Related U.S. Application Data

[63] Continuation of Ser. No. 670,371, Nov. 9, 1984, Pat. No. 4,607,643.

[51] Int. Cl.⁴ .................................................. A61B 5/02
[52] U.S. Cl. ................................... 128/715; 128/670; 128/911
[58] Field of Search ................ 128/207.15, 911, 670, 128/671, 715, 721, 725, 739, 773, 774, 780

[56] References Cited

U.S. PATENT DOCUMENTS

| 31,377 | 9/1983 | Mylrea et al. | 128/715 |
| 3,499,435 | 3/1970 | Rockwell et al. | 128/671 |
| 3,640,282 | 2/1972 | Kamen et al. | 128/207.15 |
| 3,734,094 | 5/1973 | Calinog | 128/642 |
| 3,951,136 | 4/1976 | Wall | 128/670 |
| 4,301,809 | 11/1981 | Pinchak | 128/715 |
| 4,304,239 | 12/1981 | Perlin | 128/715 |
| 4,327,720 | 5/1982 | Bronson et al. | 128/911 |
| 4,383,534 | 5/1983 | Peters | 128/715 |
| 4,475,555 | 10/1984 | Linder | 128/670 |
| 4,577,638 | 3/1986 | Graham | 128/671 |
| 4,607,643 | 8/1986 | Bell et al. | 128/911 |

Primary Examiner—Max Hindenburg
Attorney, Agent, or Firm—King & Schickli

[57] ABSTRACT

A combination endotracheal tube and stethoscope is provided so as to allow simultaneous patient ventilation and monitoring of vital sounds by a single instrument. The tracheal tube includes an inflation cuff adjacent the distal end and a longitudinal pressure conduit to inflate the cuff so as to peripherally seal the assembly against the trachea wall. An audio cuff extends at least partially coextensive and concentrically with the inflation cuff and has sufficient resiliency to vibrate in response to the patient's vital sounds. The inflation cuff comprises a highly flexible bulb in direct contact with the trachea wall and the audio cuff is a sleeve inside the bulb and spaced peripherally from the tube to allow vibration. The sleeve is sufficiently stable and maybe foam-filled to maintain the spacing even upon inflation of the bulb. Preferably, the sleeve is positioned wholly within the inflation bulb. The pressure conduit extends longitudinally along the tube and opens into communication with the inflation cuff. An audio conduit extends along the side wall and opens through a plurality of ports forming an audio manifold into the audio cuff.

8 Claims, 2 Drawing Sheets

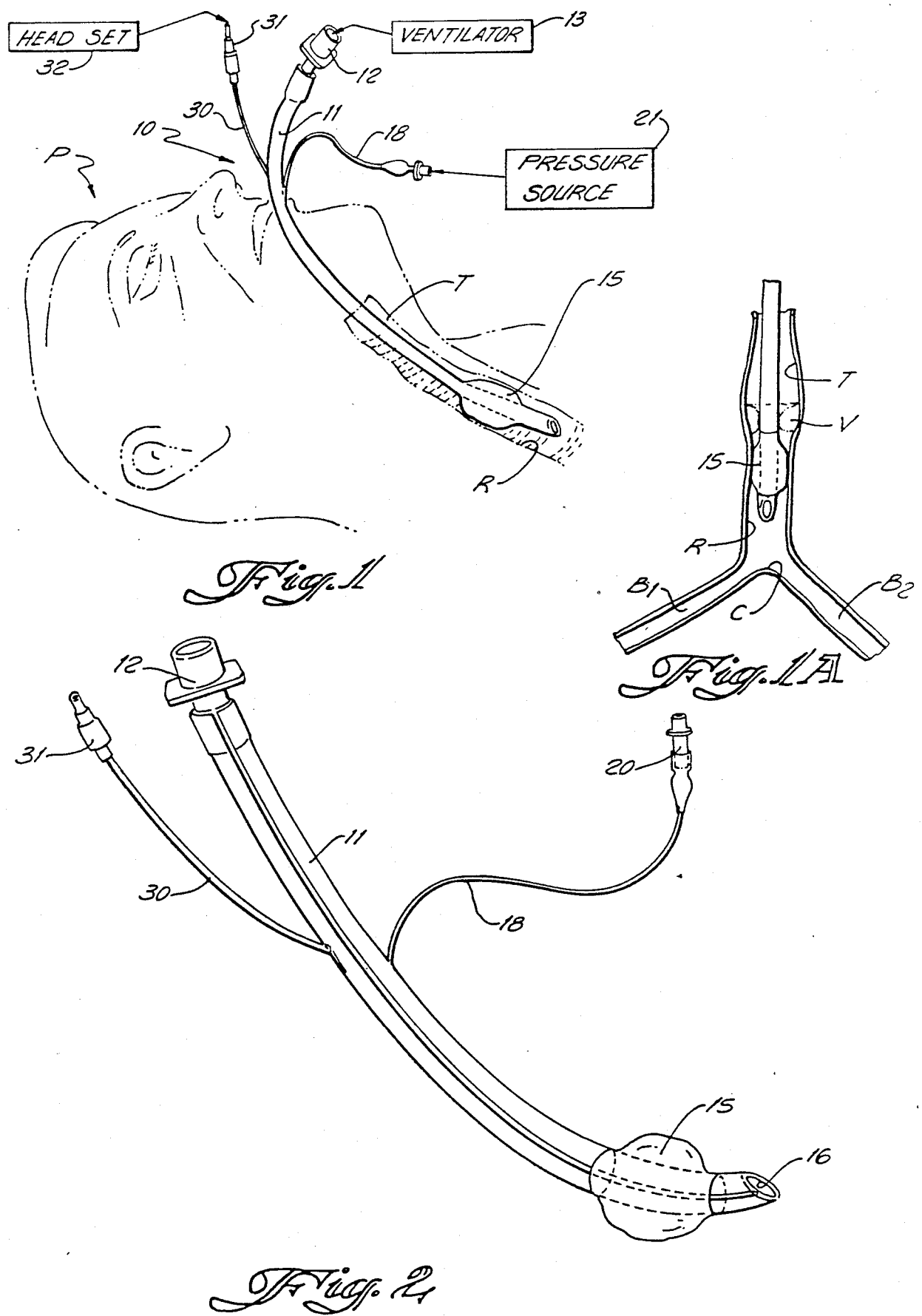

ENDOTRACHEAL TUBE/STETHOSCOPE COMBINATION

The original U.S. patent application, Ser. No. 670,371, filed Nov. 9, 1984 of which this is a continuation application, is now U.S. Pat. No. 4,607,643 issued Aug. 26, 1986.

BACKGROUND OF THE INVENTION

The present invention relates to the construction of a tracheal tube for applying anesthetic gases and oxygen to a patient, and more particularly to a tracheal tube combined with an integral stethoscope to allow more efficient monitoring of the patient's vital sounds during an operation.

BACKGROUND ART

During surgical operations, a preferred method of applying an anesthetic to a patient involves the use of a tube extending down into the trachea of the patient. The tube is inserted through the throat of the patient to a location in the trachea just below the vocal cords. At this location, an inflation cuff is pressurized in order to seal against the walls of the trachea. When this has been done, the desired intrapulmonary pressure can be established by the introduction of nitrous oxide and other anesthetic gases and oxygen. These gases are administered through a ventilator attached to the proximal end of the tube.

When an endotracheal tube is used with a small child, or in other instances where the mucous membranes lining the tracheal wall are especially sensitive, a plain tube without an inflation cuff is preferred.

In the past, with either a cuffed or uncuffed tube the vital sounds of the patient, including the breath and heart sounds, have been monitored by the anesthetist through a separate esophageal stethoscope or by a precordial stethoscope positioned over the sternum of the patient. In most instances, the precordial stethoscope is preferred since it avoids having an additional invasive instrument during the operation. However, with either of these prior art procedures, the anesthetist must deal with working with two separate instruments making sure each is properly inserted and then maintained in the proper location. In the instance of use of the separate esophageal stethoscope, the anesthetist must make some separate provision for monitoring the breath sounds of the patient. This is usually through still another instrument connected to the trachea tube outside the patient's body. Also, special care must be used to prevent irritation of the sensitive esophageal wall with the stethoscope. On the other hand, with the precordial stethoscope, it is very difficult to accurately monitor both breath and heart sounds since the stethoscope is not immediately adjacent the source of the sounds and because of outside interference. There is also the likelihood of the stethoscope being artificially disturbed by others, such as the doctor performing the operation, or the unexpected movement of the patient's body.

In an attempt to overcome the shortcomings involved in these procedures, certain improvements have been suggested. In one such improvement, the concept of providing a stethoscope on the tracheal tube in tandem with the inflation cuff has gained some success in tests. However, this concept obviously causes an increase in the length of the enlarged section of the tube at the distal end. In turn, the manufacturing process is complicated and the cost is increased. The inflation cuff is positioned below the vocal cords, and the stethoscope must then be positioned above the throat area, thus complicating the intubation process.

In another form of tracheal tube for providing anesthetic gases and oxygen to a patient, a separate electronic stethoscope transducer is carried by the tracheal tube down into the trachea. The electronic transducer is monitored by special electronic equipment attached to wires emerging from the proximal end of the tube. Because of the need for the special electronic equipment, which is expensive and requires electrical power, this arrangement has proven to be generally unsuccessful.

DISCLOSURE OF THE INVENTION

Thus, with the above shortcomings in the art in focus, it is a primary object of the present invention to provide a simplified, combined endotracheal tube and stethoscope to allow more efficient introduction of anesthetics to a patient and simultaneous monitoring of the vital sounds of the patient.

It is another object of the present invention to provide a tracheal tube/stethoscope combination providing greatly increased ease of handling and use by the anesthetist.

It is still another object of the present invention to provide an instrument for administering anesthetics and simultaneously monitoring vital sounds that is immediately ready to use after intubation and easier to maintain in the proper position throughout the operation.

It is another object of the present invention to provide a tracheal tube/stethoscope combination providing an instrument minimizing the need for invasive instruments in the body during the operation.

It is another object of the present invention to provide a combined tracheal tube and stethoscope that can be inexpensively manufactured and reduce the overall cost involved in instruments and related apparatus needed by an anesthetist.

It is still another object of the present invention to provide an endotracheal tube with an inflation cuff for sealing the trachea and an audio cuff forming a stethoscope transducer within the inflation cuff.

Additional objects, advantages and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and, in accordance with the purposes of the present invention as described herein, an improved assembly for use by an anesthetist during an operation for providing endotracheal ventilation and vital sounds monitoring by stethoscope is provided. The assembly includes a trachea tube, an inflation cuff located at the distal end surrounding the tube, means for pressurizing the cuff to seal against the trachea wall and an audio cuff extending at least partially coextensive with the inflation cuff along the tube and having sufficient resiliency to vibrate in response to patient vital sounds to permit monitoring during patient ventilation.

In the preferred embodiment shown in the drawings, the inflation cuff is on the outside so that it directly engages the trachea wall; the audio cuff being on the inside immediately adjacent the tube. Preferably, the audio cuff is positioned wholly within the inflation cuff.

A pressure conduit extends longitudinally inside the wall of the tube with a mouth opening into the inflation cuff. A pressure connector adjacent the proximal end is provided for connection to a suitable pressure source. A similar conduit extends longitudinally along and inside the wall of the tube for transmission of the sounds from the audio cuff. An audio connector adjacent the proximal end is provided for direct connection to a stethoscope headset. The tracheal tube includes a connector also adjacent the proximal end for direct connection to a ventilator for applying the anesthetic gases and oxygen to the patient.

The audio conduit opens through a plurality of ports forming an audio manifold inside the audio cuff. The audio cuff itself includes a flexible plastic sleeve that is slightly spaced from the tube to allow vibration in response to the vital sounds. The sleeve is sufficiently stable to maintain the spacing even upon inflation of the inflation cuff. In contrast, the inflation cuff is formed by a highly flexible bulb so as to provide full sealing action in the trachea with minimum pressure to enhance the audio volume from the audio cuff, and also lessen possibility of excess pressure that could harm the delicate mucous membranes of the trachea.

Since the plastic inflation cuff totally encompasses the inner audio cuff, there is a desirable reduction in uncontrolled vibration and resonating of the audio cuff to provide better sound definition. The inflation cuff also provides the optimum seal around the trachea to maintain the desired intrapulmonary pressure. The breath sounds are picked up by the audio cuff directly from the in and out flow of gases along the tube and the heart sounds are picked up directly by transmission through the inflation cuff, pressurized gas and audio cuff. With the combined tracheal tube and stethoscope of the invention, the anesthetist is able to more easily hear and distinguish the breath and heart sounds since the sound transducers are closer to the source.

Still other objects of the present invention will become readily apparent to those skilled in this art from the following description, wherein there is shown and described in more detail the preferred embodiment of this invention. This simply illustrates one of the modes best suited to carry out the invention and as will be realized the invention is capable of other different embodiments and the several details are capable of modifications in various, obvious aspects, all without departing from the invention. Accordingly, the drawings and descriptions should be regarded as illustrative in nature and not as restrictive.

BRIEF DESCRIPTION OF THE DRAWINGS

FIG. 1 is a perspective view of the endotracheal tube/stethoscope combination and related control and supply system for use on a patient;

FIG. 1A illustrates an enlargement and expanded frontal view of the trachea of the patient of FIG. 1 with the distal end of the assembly in position;

FIG. 2 is an enlarged perspective view of the endotracheal tube/stethoscope combination of the present invention;

BEST MODE OF CARRYING OUT THE INVENTION

Figure 3:
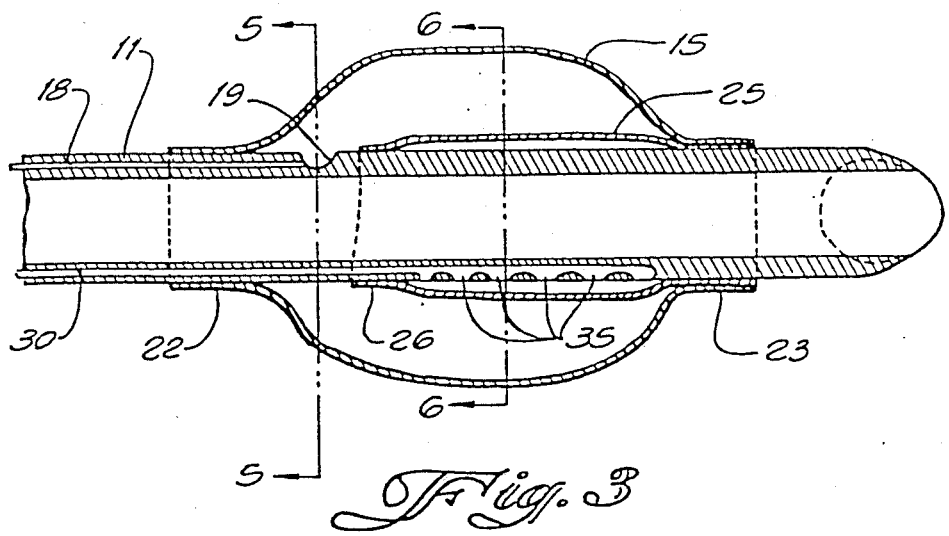
FIG. 3 is a cross-sectional view taken along the longitudinal axis adjacent the distal end of the assembly.

Reference is now made to FIG. 1, illustrating the manner in which the combined endotracheal tube/stethoscope assembly 10 is utilized on a patient P, shown in phantom line outline. Included in the assembly 10 is a tracheal tube 11, best shown in FIG. 2, with a connector 12 for connection to ventilator 13 (see FIG. 1). The distal end of the tube 11 includes an inflation cuff 15 surrounding the tube 11 and an adjacent opening 16 for supplying the anesthetic gases (such as nitrous oxide) and oxygen to the pulmonary system of the patient.

The tracheal tube 11, as well as the other components of the assembly 10, are made of surgical grade plastic in accordance with the rigid governmental standards that are applicable. The assembly 10 is, of course, sold only in a sterilized pouch and is designed for one use only. The lip around the opening 16 is rounded and smooth in order to prevent injury to the patient's delicate membrane surfaces.

The inflation cuff 15 is inflated by pressurized gas, such as pressurized ambient air. This gas is supplied through a pressure conduit 18 extending along the wall of the tube 11, as best shown in FIG. 3. The distal end of the pressure conduit 18 opens into the chamber within the cuff 15 through a mouth 19. As shown in FIG. 2, the conduit 18 emerges from the tube 11 at a location partially along the tube's length and is provided with a pressure connector 20 at the proximal end. As shown in FIG. 1, the pressure connector is connected to a suitable pressure source 21 and upon activation the pressurized gas fills the chamber and inflates the cuff 15 (see FIG. 3).

In the preferred embodiment, the cuff 15 takes the form of a bulb that is substantially concentric with the tube 11. The two ends of the cuff 15 are heat sealed around the outside against the tube at heat seal areas 22, 23, thus forming a gas tight chamber. An audio cuff 25 is formed on the tube 11 in the same region. Specifically, the audio cuff 25 is at least partially coextensive with the inflation cuff 15 along the tube. The cuff 25 is preferably a sleeve with one end attached to the tube by sealing under the inflation cuff 15 in seal area 23, and a separate seal area 26 inside the inflation chamber (see FIG. 3).

Figure 4:
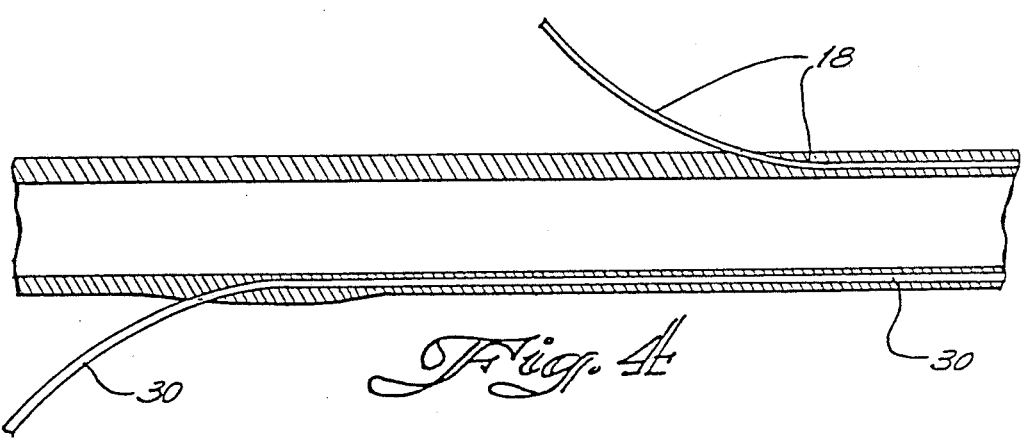
FIG. 4 is a cross-sectional view taken longitudinally along the tracheal tube showing the emergence of the pressure and audio conduits.

As will be thus realized, in the preferred embodiment, the audio cuff 25 is positioned wholly within the inflation cuff 15. Running to the audio cuff 25 is an audio conduit 30 (see FIGS. 3 and 4). As is evident in FIG. 2, the conduit 30 is integral with the side wall of the tube 11 until a point substantially midway where the conduit 30 emerges, finally terminating at the proximal end in audio connector 31. A suitable headset 32 is attached, as depicted in FIG. 1.

The opening of the audio conduit 30 to the chamber within the audio cuff 25 takes the form of a plurality of spaced ports 35 forming in effect an audio manifold (see FIG. 3). With this arrangement, upon vibration of the audio cuff 25, the sound waves can freely enter the manifold, travel up through the conduit 30 and connector 31 to the headset 32 of the anesthetist. As will be apparent, the sound detection is exceptional with this arrangement.

In use, the tube 11 is inserted into the mouth of the patient P, substantially as shown in FIG. 1. The tube 11 and the deflated cuff 15 travel easily through the throat T and past the vocal cords V (see FIG. 1A, also). With the cuff 15 now in the trachea R of the patient P, the pressure source 21 can be immediately activated, the cuff 15 inflated and the anesthetic gases and oxygen can be immediately administered.

As shown in FIG. 1A, the distal tip of the tube 11 is in this position well above the carina C between the left bronchus $B_1$ and the right bronchus $B_2$. With the trachea R thus sealed, the pulmonary pressure can be properly established and maintained for the duration of the operation.

Thus, in the preferred embodiment, the inflation cuff 15 is on the outside and directly engages the peripheral wall of the trachea R. From this direct engagement, heart sounds emanating from within the body from surrounding arteries and the heart itself are transmitted into pulsations within the chamber formed by the cuff 15. The pressurized gas in turn transmits these pulsations to the auditory cuff 25; the sound waves then traveling through the manifold of ports 35, the conduit 30 and eventually to the ears of the anesthetist. Advantageously, the audio cuff 25 faithfully picks up the pulsating sounds free of noise background. The arrangement substantially reduces uncontrolled vibration and resonating that occurs in instances where a separate stethoscope is used.

In addition to monitoring the heart sounds, the cuff 25 allows monitoring of the bi-directional breath sounds as the gases pass back and forth through the inside of the tube 11. It is proven to be highly advantageous to have both vital sounds of the patient P being picked up by the same audio transducer, that is, the cuff 25. The anesthetist quickly recognizes and can faithfully monitor both sounds in order to assure maximum safety of the patient.

Figures 5, 6, 7:
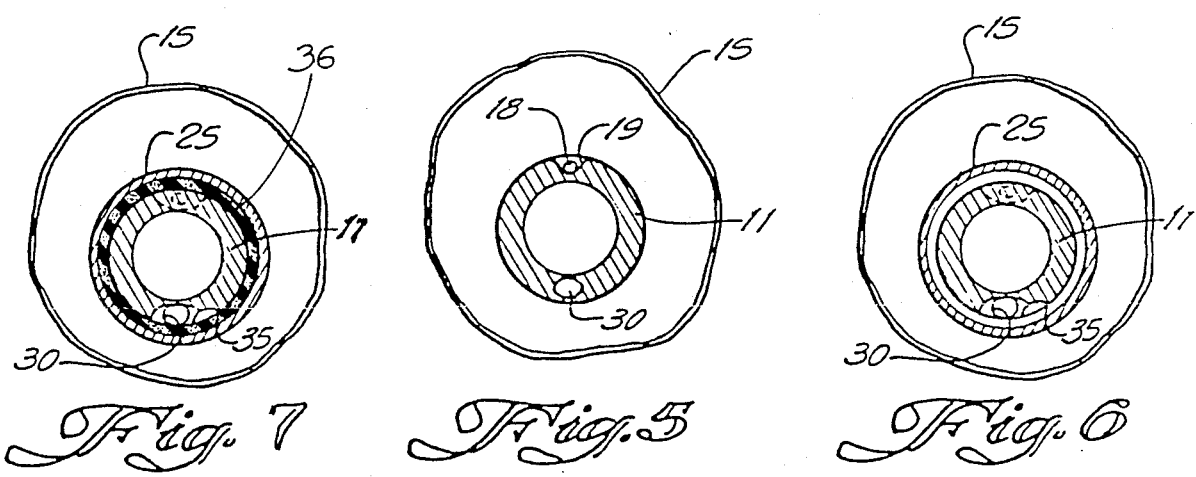
FIG. 5 is a lateral cross-sectional view taken along line 5—5 of FIG. 3 and showing the mouth opening to the inflation cuff.
FIG. 6 is a cross-sectional view taken along lines 6—6 of FIG. 3 showing the audio cuff within the inflation cuff and the opening of the audio manifold.
FIG. 7 is a cross-sectional view of a modification of the invention wherein resilient foam is positioned under the audio cuff.

The audio cuff 25 is formed of a flexible plastic sleeve and is slightly spaced from the tube 11, as shown in FIGS. 3 and 6, in order to allow vibration in response to the vital sounds. The plastic material and the thickness is selected so that the sleeve is sufficiently stable to maintain the spacing around the periphery of the tube 11 even upon pressurization of the chamber surrounding the sleeve as the inflation cuff 15 is inflated. On the other hand, the plastic bulb forming the inflation cuff 15 is highly flexible compared to the sleeve. The flexibility assures optimum sealing engagement with the wall of the trachea R using minimum gas pressure. This fact assists in keeping the audio cuff 25 from collapsing against the outer wall of the tube 11.

Also, of particular importance is the provision of a plurality of ports 35 forming a manifold at the end of the conduit 30. These ports allow free entry of the sound vibrations that then travel up through the conduit 30 and are heard in an unimpeded fashion by the anesthetist.

In summary, a combined endotracheal tube/stethoscope assembly 10 has been provided, that is, simple in construction and extremely efficient in use. In particular, it is easier for the anesthetist to use and handle. It avoids a second invasive instrument with the problems attendant thereto, and is not position sensitive, as with the use of the precordial stethoscope. Introducing a general anesthetic gas into a patient is a very complex procedure requiring numerous separate motions and actions, and the freedom afforded the anesthetist by combining the two functions into one instrument results in a major step forward in the art.

In addition, from actual tests, the heart and breath sounds are easier to hear and distinguish with the endotracheal tube/stethoscope assembly 10 of the present invention. The inner audio cuff 25 picks up the sounds that are close by and transmits them faithfully to the headset 32 of the anesthetist. Uncontrolled vibration and resonating of the sounds are essentially eliminated.

The audio cuff 25 is sufficiently stable to maintain the spacing and the sound pick-up is efficiently transmitted through a plurality of ports 35 forming a manifold. The inflation cuff 15 is, on the other hand, highly flexible compared to the audio cuff 25 so as to provide full sealing action with minimum pressure around the trachea wall. This feature assures properly controlled intrapulmonary pressure, but at the same time minimizes any chance of injury to the sensitive mucous membrane of the trachea R by excessive pressure.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, a full peripheral sound chamber can be formed in the surface of the tube 11 under the audio cuff 25 and/or resilient foam 36 (see FIG. 7) may be positioned under the cuff 25 in order to enhance the vibrating action and prevent any tendency to collapse against the tube 11. Also, the inflation cuff may, if desired, be positioned inside the audio cuff to provide direct engagement of the audio cuff with the trachea. In this instance, the audio cuff may be slightly pressurized and/or foam-filled, (see foam 36) to provide resiliency, as suggested above. It will thus be realized that the preferred embodiment was chosen and described to provide the best illustration of the principals of the invention and its practical application to thereby enable one of ordinary skill in the art to utilize the invention and various embodiments and with various modifications as are suited to the particular use contemplated. It is intended that the scope of the invention be defined by the claims appended hereto.

We claim:

1. An assembly for providing endotracheal ventilation and vital sounds monitoring by stethoscope in a patient comprising
   a tracheal tube;
   means for substantially peripherally sealing the assembly against the trachea wall adjacent the distal end of the tube inserted in the trachea;
   means for providing ventilation to the trachea through said tube; and
   an audio cuff extending along the tube at least partially coextensive with said sealing means and having sufficient resiliency to vibrate in response to patient vital sounds to permit monitoring during patient ventilation.

2. The assembly of claim 1 wherein said tube includes a side wall and wherein is provided an audio conduit extending longitudinally along the side wall of said tube and opening into said audio cuff.

3. The assembly of claim 2 wherein the opening to the audio cuff is provided by a plurality of ports forming an audio manifold at the distal end of said audio conduit in said audio cuff for placement inside the trachea.

4. The assembly of claim 2 wherein said audio cuff includes a flexible plastic sleeve extending around the periphery of the tube.

5. The assembly of claim 4 wherein said sleeve is slightly spaced from said tube providing a spacing to allow vibration in response to the vital sounds.

6. The assembly of claim 5 wherein said sleeve is sufficiently stable to maintain the spacing around the periphery of the tube.

7. The assembly of claim 5 wherein is provided resilient foam in said sleeve to maintain the spacing around the periphery of the tube in order to enhance the vibrating action and prevent any tendency to collapse.

8. The assembly of claim 2 wherein said tube includes a vent connector adjacent the proximal end outside the trachea for direct connection to a ventilator and an audio connector adjacent the proximal end of said audio conduit for direct connection to a stethoscope head set.

* * * * *